United States Patent

Mihaylov et al.

Patent Number: 5,364,593
Date of Patent: Nov. 15, 1994

[54] DIRECT-READ COLORIMETRIC EXPOSIMETER

[76] Inventors: Gueorgui M. Mihaylov, 900 Piney Branch Dr., Virginia Beach, Va. 23451; Kirollos S. Kirollos, 1502 Canterford Ct., Virginia Beach, Va. 23464; Kevin L. Lockerby, 1017 Woodsmans Reach, Chesapeake, Va. 23320

[21] Appl. No.: 96,303

[22] Filed: Jul. 26, 1993

Related U.S. Application Data

[63] Continuation-in-part of Ser. No. 969,762, Oct. 30, 1992, abandoned.

[51] Int. Cl.⁵ .................................. G01J 1/48
[52] U.S. Cl. .................................. 422/87; 422/55; 422/57; 422/58; 422/86; 422/83; 422/88; 435/807; 436/165; 436/169; 436/170; 436/805
[58] Field of Search ............ 422/86, 87, 5.8, 93, 422/55-60, 83; 436/805, 165, 170, 164, 902, 169; 435/805, 807

[56] References Cited

U.S. PATENT DOCUMENTS

| | | | |
|---|---|---|---|
| 3,924,219 | 12/1975 | Braun | 422/83 X |
| 3,950,980 | 4/1976 | Braun et al. | 422/83 X |
| 3,985,017 | 10/1976 | Goldsmith | 422/83 X |
| 4,205,043 | 4/1980 | Each et al. | 422/56 |
| 4,235,097 | 11/1980 | Kring et al. | 73/23 |
| 4,256,694 | 3/1981 | McAllister et al. | 422/58 |
| 4,271,121 | 5/1981 | Diller et al. | 422/56 |
| 4,478,792 | 10/1984 | McConnaughey et al. | 422/56 |
| 4,666,859 | 4/1987 | Attar | 436/130 |
| 4,772,560 | 9/1988 | Attar | 436/165 |
| 4,780,282 | 10/1988 | Holtzclaw et al. | 422/56 |
| 4,826,772 | 5/1989 | Meathrel | 436/93 |
| 4,840,919 | 5/1989 | Attar | 436/111 |
| 4,904,449 | 2/1990 | Heckmann | 422/87 |

FOREIGN PATENT DOCUMENTS

35871 7/1984 Bulgaria .

*Primary Examiner*—James C. Housel
*Assistant Examiner*—Long V. Le
*Attorney, Agent, or Firm*—E. Lieberstein

[57] ABSTRACT

A direct-read exposimeter for providing a visual, graded measurement of color variation corresponding to different ranges of dosage exposure to a polluting gas in the atmosphere over a given time period. The exposimeter includes a color-forming member and at least one gas-diffusion control member within an enclosure formed between a base and a cover. The cover has a number of openings exposed to the atmosphere in alignment with a number of separate diffusion zones formed in the gas-diffusion control member.

19 Claims, 7 Drawing Sheets

Figure 4a
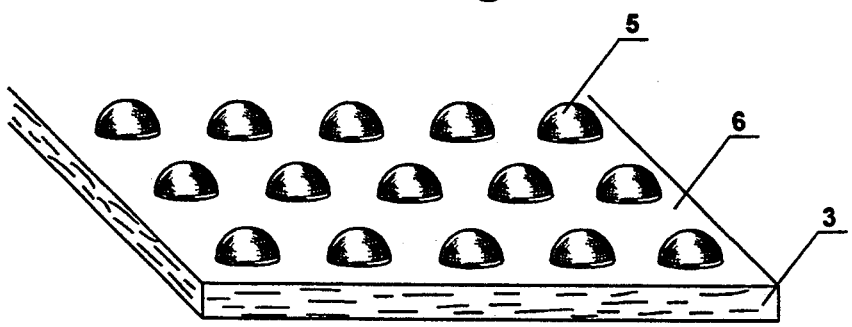
Figure 4
Figure 4b
80%
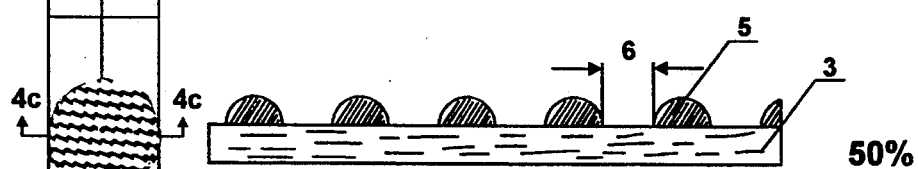
Figure 4c
50%
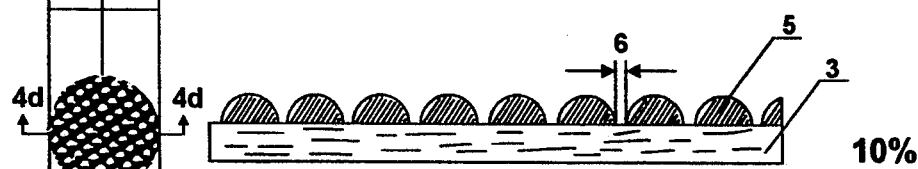
Figure 4d
10%
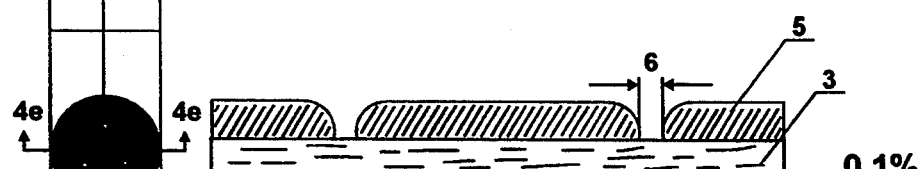
Figure 4e
0.1%

L = D

L < D

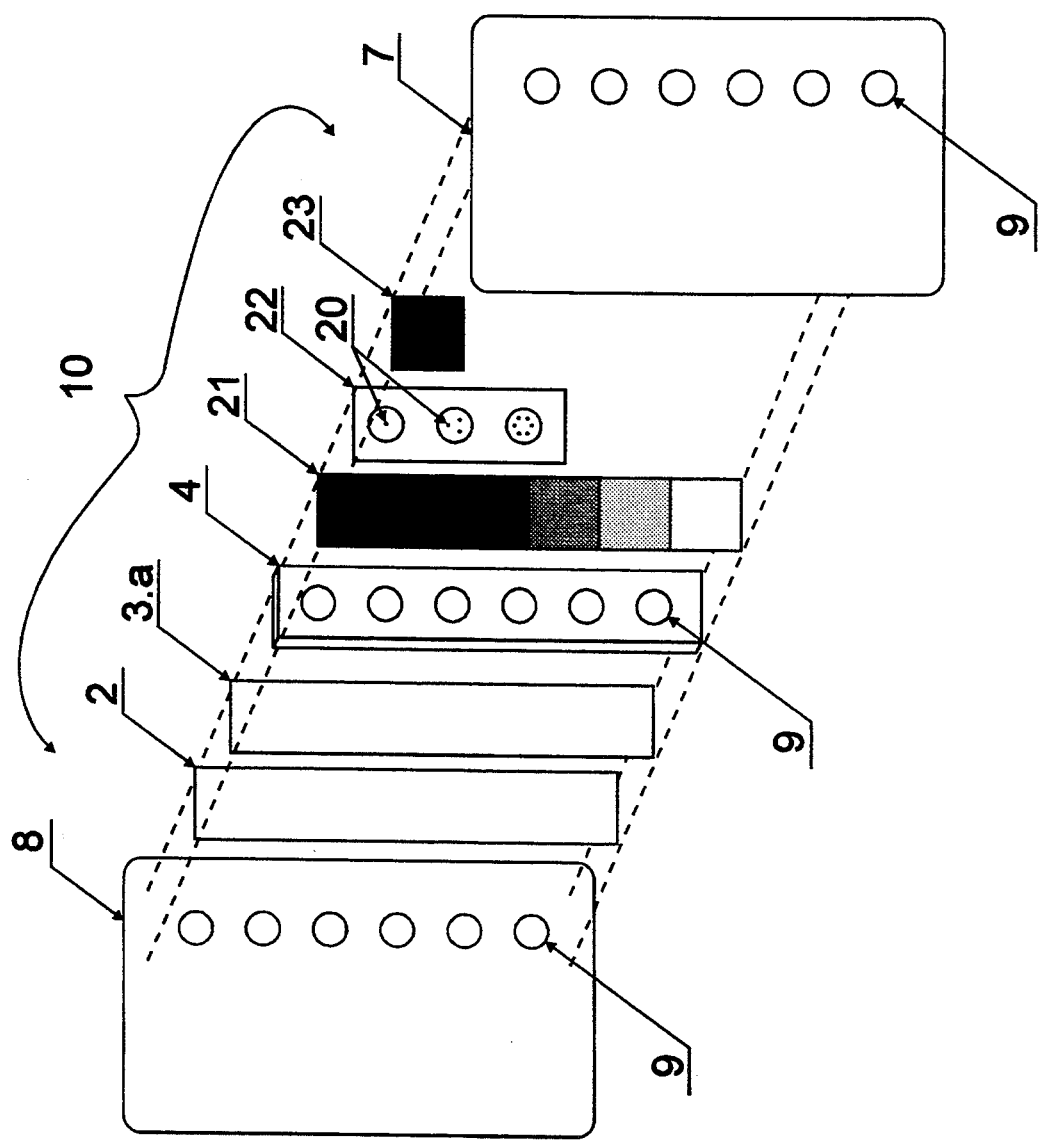

5,364,593

DIRECT-READ COLORIMETRIC EXPOSIMETER

FIELD OF THE INVENTION

This is a continuation in part of U.S. patent Ser. No. 07/969,762, filed Oct. 30, 1992, now abandoned and relates to a direct-read, passive, colorimetric exposimeter which may readily be carried by an individual for performing a real-time measurement of the exposure level of a gas/vapor pollutant in the ambient atmosphere.

BACKGROUND OF THE INVENTION

There is a need in the field of industrial hygiene for a colorimetric, passive device, which may be carried by an individual in the form of a badge, to provide a direct-read quantitative measurement of the range of concentration of various toxic gases and/or vapors in the ambient atmosphere, by means of real-time integration of the exposure level of such toxic gases or vapors over a fixed time horizon.

Several methods are presently known for the colorimetric estimation of time-weighted average (TWA) measurements and the short-term exposure limit (STEL) of toxic gases and vapors in the atmosphere. These methods can be classified into the following major categories:

1. Methods which compare the quality of a received colorimetric result (density, color, tone, shade, or nuance) to a given color standard. The colorimetric devices of this category rely on a gas pollutant reacting chemically with reagent(s) dispersed on a suitable substrate to produce a color change. The estimation of the gas pollutant is semiquantitative and is reliable only for a relatively narrow exposure interval.

2. Methods which use the quantity of the received color expressed by area or length of stain. In general, the devices in this category are made of transparent tubes filled with a granular, solid support impregnated with colorimetric reagent(s). Gas pollutants penetrate by diffusion through a diffusion retainer and react with the colorimetric reagent(s). The colorimetric result is a length of stain proportioned to the total exposure value of the concentration multiplied by the exposure time, i.e., CT value. The measure of exposure is visual and occurs by comparing the length of the stain to a fixed scale. Although this is a significant advantage, such devices are nonlinear and their response time changes with the length of stain.

Several passive, direct-read, colorimetric devices have been proposed in the patent literature, which rely upon the degree of gas penetration through the chromophoric reagent to determine dosage exposure, and to visually, provide a graded sensitivity in the color detection for real-time measurement. In the dosimeter of U.S. Pat. No. 4,478,792, issued to McConnaughy, a stack of porous sheets are impregnated with a reagent, causing the sheets in the stack to sequentially change color upon exposure to a gas pollutant relative to the degree of gas penetration. The degree of gas penetration is a function of the gas concentration in the atmosphere over a given time period. By removing the sheets at the end of the time period, the last color-changed sheet corresponds to the highest dosage exposure level. This is a cumbersome and impractical way to measure dosage exposure, as well as being unreliable. In U.S. Pat. No. 4,271,121, issued to Diller, et al., the indicator layer containing the colorimetric reagent is subdivided into a plurality of measuring fields. A graded sensitivity in color detection is achieved, using a plurality of membranes of filter paper superimposed over the indicator layer in a staggered relationship, or by using different membrane thicknesses. The variation in membrane thickness or the staggered membrane arrangement varies the diffusion resistance to the separate measuring fields in the indicator layer and, accordingly, the degree of gas penetration to each measuring field which, in turn, varies the level of dosage exposure in each of the measuring fields. In theory, the arrangement, as taught by Diller, will provide a rapid visual, quantitative recognition of dosage exposure by providing different exposure ranges correlated to the different measuring fields. However, the range of color sensitivity is much too limited for practical use because the thickness of the membranes or the staggered arrangement of membranes needed to distinguish one measuring field from another varies in a geometric progression. Since a multiple number of measuring fields would be necessary to cover a reasonable exposure range for any known polluting gas, the variation in thickness or number of membranes would make the device unwieldy and far too expensive to manufacture.

SUMMARY OF THE INVENTION

The direct-read, passive, colorimetric exposimeter of the present invention provides a visual graded measurement of color variation over a wide concentration range, corresponding to the range of permissible exposure over a predetermined time period, as proscribed by OSHA, for any given polluting gas. Typical polluting gases for which OSHA has proscribed exposure limits include, e.g., $H_2S$, $Cl_2$, $SO_2$, hydrazine, ammonia, and acetone. By providing a visual, graded measurement of color variation, the exposimeter of the present invention supplies a quantitative indication of the range of toxic exposure corresponding to the average concentration of the gaseous contaminant under examination over a given exposure time period.

The direct-read colorimetric exposimeter of the present invention operates as both a detection badge for detecting a specified polluting gas in the ambient atmosphere and for providing a visual graded measurement of color variation corresponding to different ranges of exposure to such polluting gas over a given time period. The exposimeter of the present invention broadly comprises: a base composed of a gas-impermeable, inert material; a cover for said base composed of a gas-impermeable, inert material, with said cover secured to the base along preselected edges to form an enclosure; a color-forming member located in said enclosure adjacent to said base, said color-forming member containing a chromophoric reagent which changes color when exposed to said polluting gas; and at least one gas-diffusion control member disposed between said color-forming member and said cover, with said gas-diffusion control member composed of a porous medium having a multiplicity of solid, nonporous ink spots disposed on said porous medium in an arrangement defining a predetermined number of separate diffusion zones, with each diffusion zone having a preselected diffusion resistance corresponding to the density of ink spots in said zone, and with said cover having a number of openings in alignment with each of said diffusion zones for exposing each of said diffusion zones to the ambient atmosphere.

An alternate embodiment of the exposimeter of the present invention comprises: a base composed of a gas-impermeable, inert material; a cover for said base composed of a gas-impermeable, inert material, with said cover secured to the base along preselected edges to form an enclosure; a color-forming member located in said enclosure adjacent to said base, said color-forming member containing a chromophoric reagent which changes color when exposed to said polluting gas; and at least one gas-diffusion control member disposed between said color-forming member and said cover, with said gas-diffusion control member composed of a nonporous medium having multiple pinholes in an arrangement defining a selected number of separate diffusion zones, with at least one pinhole in each such diffusion zone, with each pinhole having a maximum (diameter) size of 0.6 mm, and with each diffusion zone having a predetermined diffusion resistance based upon the number and size of the pinholes in each such zone, respectively.

Another alternate embodiment of the exposimeter of the present invention comprises: a base composed of a gas-impermeable, inert material; a cover for said base composed of a gas-impermeable, inert material, with said cover secured to the base along preselected edges to form an enclosure; a color-forming member located in said enclosure adjacent to said base, said color-forming member containing a chromophoric reagent which changes color when exposed to said polluting gas; and at least one gas-diffusion control member disposed between said color-forming member and said cover, with said gas-diffusion control member composed of a porous medium having multiple nonporous ink spots for defining at least one diffusion zone having a diffusion resistance corresponding to the density of ink spots in said zone, and a nonporous medium having one or more diminutive pinholes, with a maximum pinhole (diameter) size below 0.6 mm, for defining at least one other diffusion zone having a diffusion resistance based upon the number and size of said pinholes in said zone.

BRIEF DESCRIPTION OF THE DRAWINGS

Other objects and advantages of the present invention will become apparent from the following detailed description of the invention, when read in conjunction with the accompanying drawings, of which:

FIG. 4 is a front view of the gas-diffusion control member in one embodiment of the exposimeter of the present invention;

FIG. 4A is a diagrammatic view in perspective of a section of any one of the diffusion zones on the gas diffusion control member of FIG. 4;

FIGS. 4B–4E are cross-sectional view taken along the lines 4b—4b; 4c—4c; 4d—4d; and 4e—4e of FIG. 4, respectively;

FIG. 8 is another exploded view in perspective of the assembly of the exposimeter of the present invention for yet another embodiment of the present invention.

DETAILED DESCRIPTION OF THE INVENTION

Figure 1:
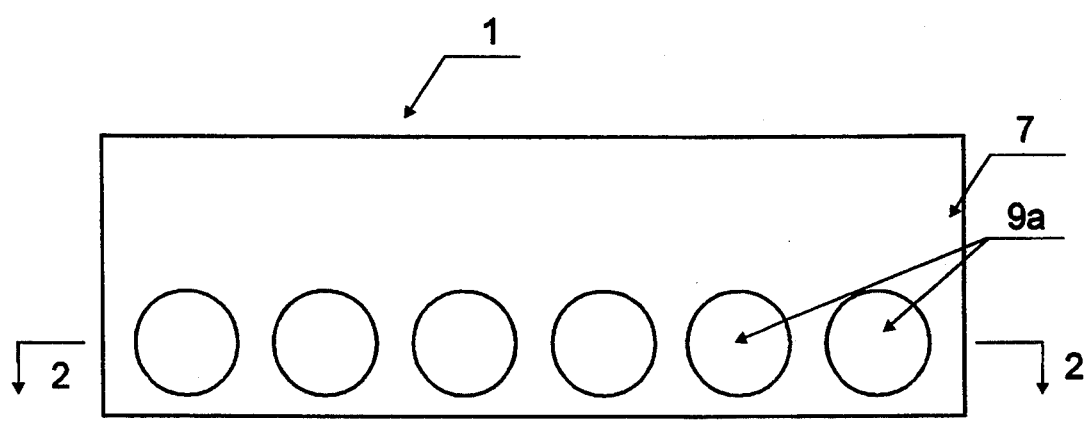
FIG. 1 is a plan view of the top side of the passive, direct-read exposimeter of the present invention.
Figure 2:
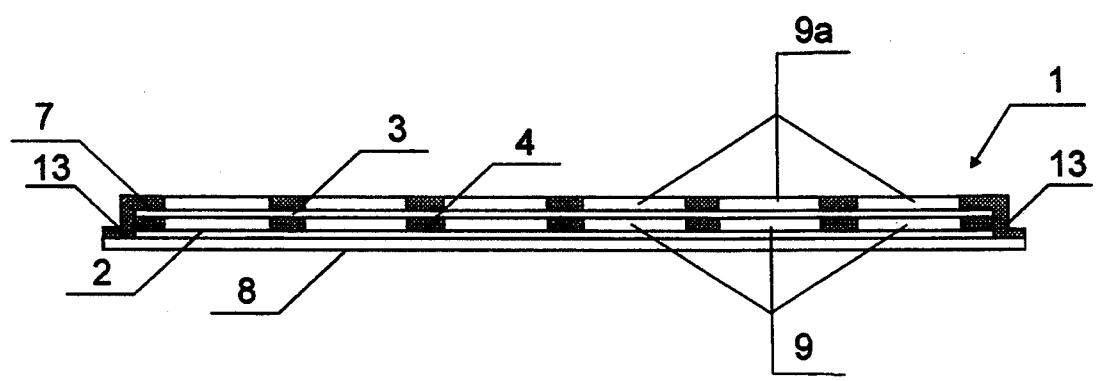
FIG. 2 is a cross-sectional view of the exposimeter of the present invention taken along the lines 2—2 of FIG. 1.
Figure 3:
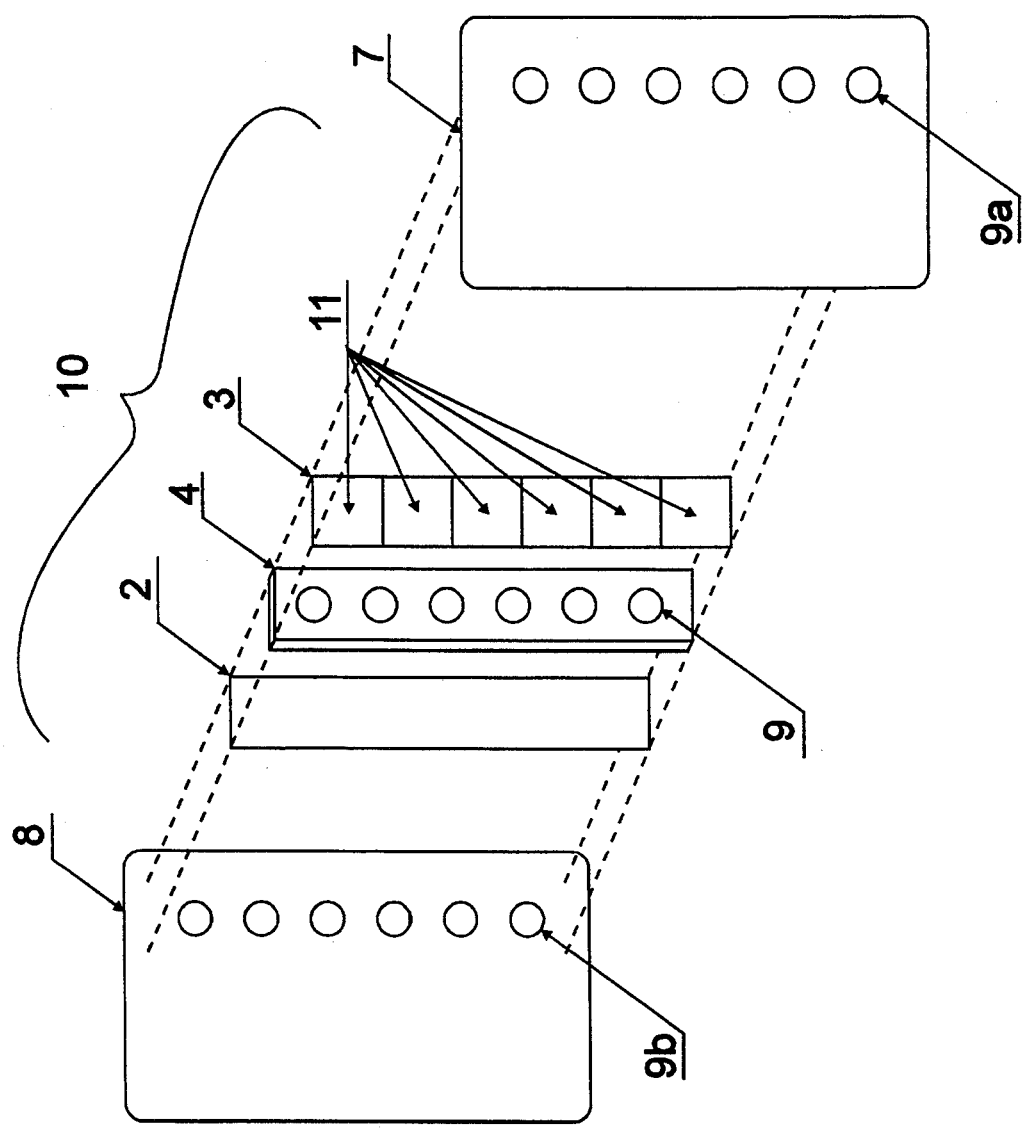
FIG. 3 is an exploded view in perspective of the assembly of the exposimeter of FIGS. 1 and 2.

The passive exposimeter (1) of the present invention, as illustrated in FIGS. 1–8, inclusive, is thin, light in weight, and rectangular in shape, although any geometry would be acceptable, provided it may be easily worn on the clothing of a person, as one would wear a badge over any desired time period to determine a time-weighted average concentration value of dosage exposure within a plurality of narrow ranges, as hereafter explained in more detail. The exposimeter (1) includes a top cover (7) of a gas-impermeable, inert material, preferably of plastic composition such as polyethylene, polyester, polypropylene, etc., and an underlying base (8) of a similar inert, plastic composition. The base (8) may be a single sheet of plastic or a plastic laminate of multiple sheets to provide reasonable thickness for use in structurally supporting the exposimeter (1). The top cover (7) is secured to the base (8) along the peripheral edges (13) of each member, preferably by glue or heat sealing the edges (13), to form an enclosure (10), as more clearly shown in FIG. 3.

Within the enclosure (10) is a color-forming indicator (2), at least one gas-diffusion control member (3), and an optional flexible member (4) with each member superimposed upon one another. The flexible, plastic member (4) is composed, preferably, of nonporous plastic of predetermined thickness, and contains an array of openings (9), preferably linearly arranged in series, so that the member (4) may represent a flat, narrow strip of plastic which is substantially smaller in width than the width of the top cover (7) and the base (8). The gas-diffusion control member (3) may also be a narrow strip of material which is subdivided into separate diffusion zones (11), which may be formed in accordance with alternate embodiments of the present invention, as discussed hereinafter in connection with FIGS. 4–8. The top cover (7) and the base (8) also contain an array of openings (9a) and (9b) which are arranged in alignment with the openings (9) in the plastic member (4), and in alignment with the diffusion zones (11) of the gas-diffusion control member (3). It should be noted that the openings 9, 9a, and 9b may be arranged in alignment with one another to form other geometrical patterns, all of which are within the scope of the present invention. If the base (8) is transparent, the openings (9b) are unnecessary.

The color-forming indicator (2) is preferably a flat strip positioned adjacent to the base (8) and contains the chromophoric reagent chemical which changes color when exposed to a specific polluting gas in the ambient atmosphere. The color indicator (2) may be constructed from any porous material, including paper, plastic, and fabric, impregnated with the chromophoric reagent. Alternatively, the reagent chemical can be coated onto a substrate carrier medium, with the coating of chemical reagent facing the top cover (7) of the exposimeter (1). The composition of the chemical reagent is selected based upon the polluting gas to be detected. Accordingly, if the polluting gas is $H_2S$, The chemical reagent may be a composition containing, e.g., lead acetate, which, as is well-known, will react with $H_2S$ to form lead sulfide, in like manner, a different chemical reagent, known to those skilled in the art, would be used to detect other polluting gases, such as $Cl_2$, $NH_4$, acetone, etc.

Figure 5:
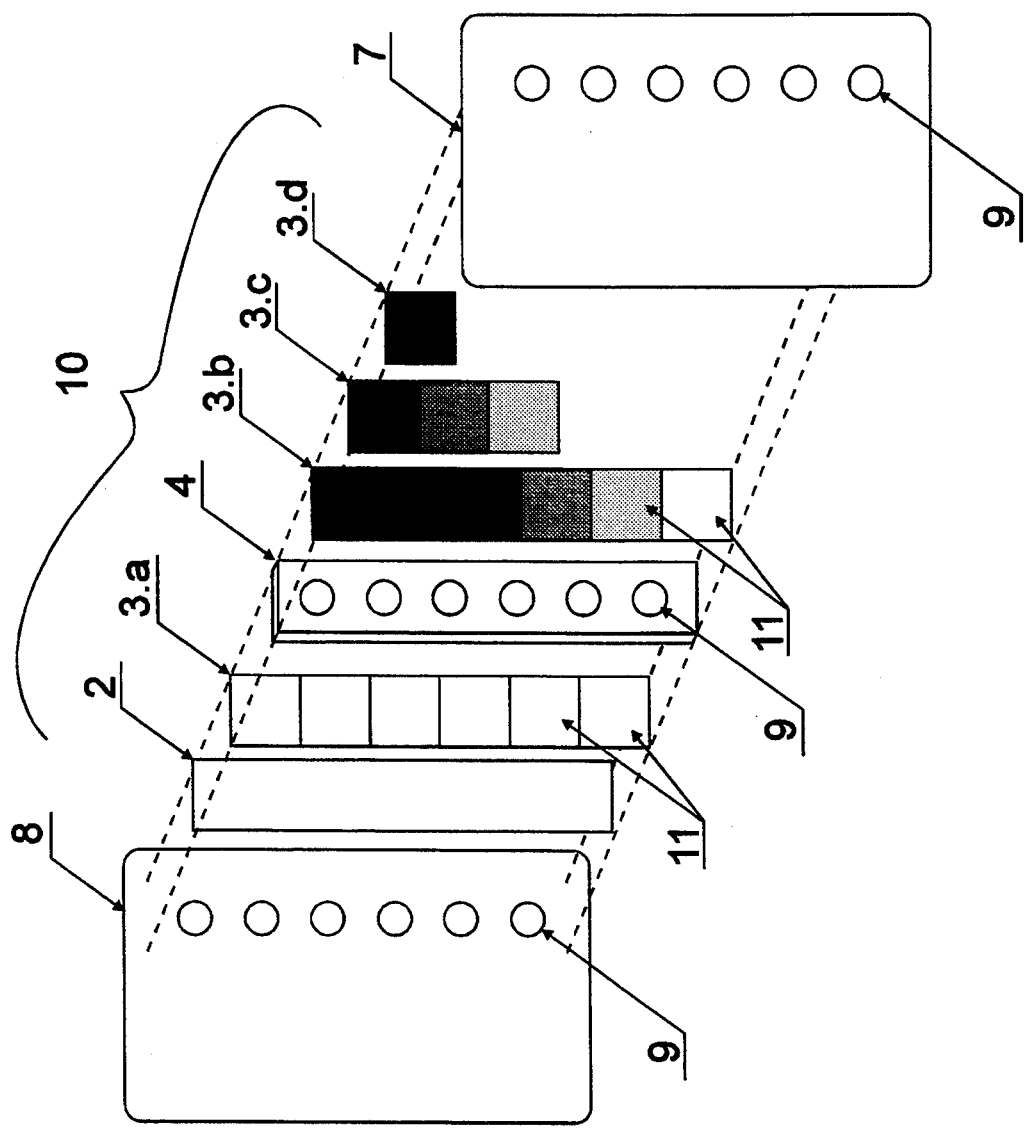
FIG. 5 is an exploded view in perspective of the exposimeter of the present invention, similar to that of FIG. 3, with an arrangement containing a plurality of gas-diffusion control members.

The presence of at least one gas-diffusion control member (3) with a multiple number of diffusion zones (11) is essential to the present invention. The diffusion zones (11) in the gas-diffusion control member (3), should correspond in number to the number of openings (9) in member (4) and to the number of openings (9a) in the top cover (7). In one embodiment of the present invention, the control member (3) is composed of a porous material, such as paper, upon which ink spots (5) are printed and cured so as to form nonporous ink spots (5), as shown in FIGS. 4 and 4A–4E, respectively. The density of the ink spots (5) in each of the diffusion zones (11) determines the diffusion resistance of each of the diffusion zones, respectively. The arrangement of the ink spots (5) and the spacing (6) between the ink spots (5) forms a pattern corresponding to halftone printing, which is used to distinguish each of the diffusion zones (11) from one another. The density of the ink spots (5) may be varied by varying the size of the ink spots (5) with equal spacing (6) between the ink spots, or the spacing (6) may be varied, as shown in FIGS. 4B to 4D, with the size of each ink spot fixed, or both may be varied. Although any conventional method of printing may be used to form the nonporous spots (5), including screen printing, the preferred method is "thermoprinting," as is known to those skilled in the printing art, which is a conventional process for curing printing ink, preferably printed by offset lithography, To form a raised ink pattern with a texture simulating engraving. The ink must become nonporous upon solidification, either by thermal or ultraviolet heat treatment, and/or by catalytic treatment with chemicals, as presently used by those skilled in the printing art. The solid ink spots (5) formed by thermoprinting have been shown, in accordance with the present invention, to be nonporous. Any conventional printing ink which will form nonporous spots (5) may be used. The density of the ink spots (5) in each of the diffusion zones (11) may be varied to satisfy any desired diffusion resistance between, extending from zero percent (0%) resistance to one hundred percent (100%), as is evident from FIGS. 4B to 4E, inclusive. The degree of diffusion through each of the diffusion zones (11) is thus easily controlled to provide as wide a variation in sensitivity as is needed to correspond to any exposure dosage range for most polluting gases, The embodiment of FIG. 3 may be modified by using a plurality of control members (3), as shown in FIG. 5, with each of the separate control members (3) identified by reference numbers 3a, 3b, 3c, and 3d, respectively. The strip (3a) is of uniform porosity. An example of the present invention, using the embodiment of FIG. 5 for detecting ammonia, is hereinafter described as Example I. Greater control of the diffusion resistance is achieved with an arrangement of overlapping diffusion control members (3).

EXAMPLE I

The exposimeter (1) of FIG. 5, comprises a base (8) and a cover (7), approximately 2-inch×3.5-inch and 1/16-inch thick, for forming an enclosure (10) exposed through the openings (9a) in the cover (7). The enclosure consists of a color-forming indicator member (2), a gas-diffusion control member (3a) with uniform porosity along all diffusion zones (11), and three additional diffusion control members (3b), (3c), and (3d), and a 1/32-inch thick, flexible plastic member (4) with each of the openings (9) preferably round ¼-inch in diameter. The diffusion control member (3a) has six diffusion zones (11), with diffusion resistance ranging from ten percent (10%) to one hundred percent (100%), overlapping the openings, diffusion member (3c) has three diffusion zones, with diffusion resistance ranging from thirty percent (30%) to seventy percent (70%), and the diffusion control member (3d) has only one diffusion zone with twenty percent (20%) diffusion resistance. Enclosure is encapsulated between the top cover (7) and the base (8). The openings (9a) and (9b) are in alignment with the diffusion zones (11) of the gas-diffusion control members (3a–3d), and with the openings (9) in the member (4). The base may be of transparent, nonporous plastic and, as such, need not have any openings (9b).

The color-forming indicator member (2) is based on the color change of $Fe(SCN)_2$, from reddish-brown to colorless by formation of a colorless complex with ammonia. The exposure range is from 4 ppm per hour to 300 ppm per hour.

Figure 6:
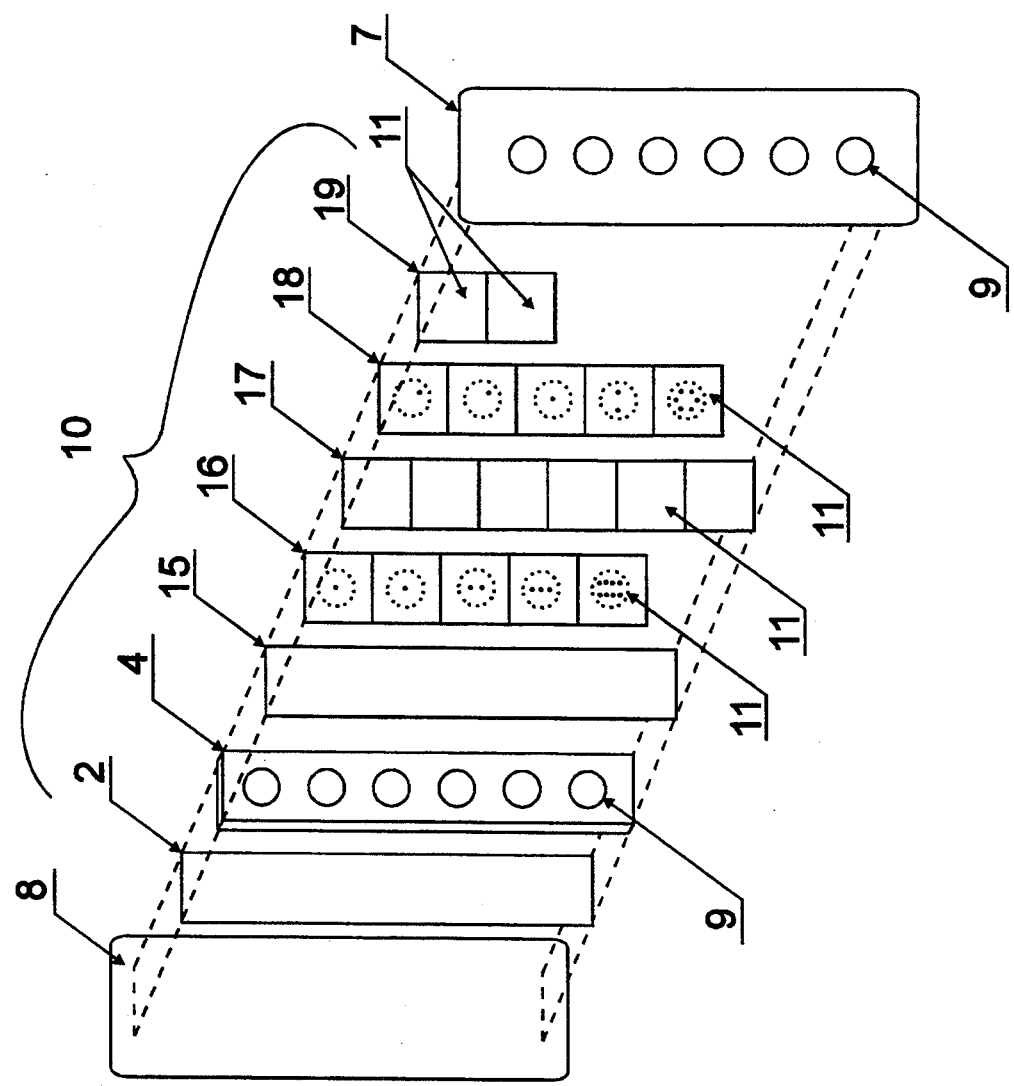
FIG. 6 is another exploded view in perspective of the exposimeter of the present invention showing another alternate embodiment of the gas-diffusion control member.
Figure 7A:
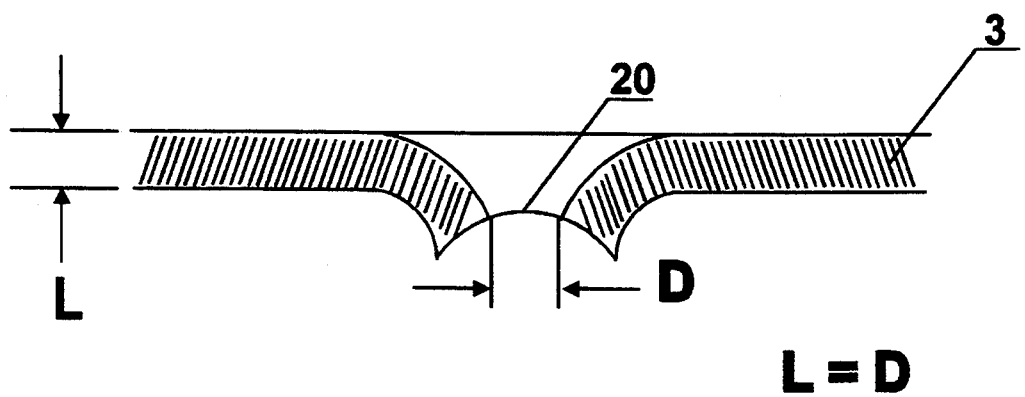
FIGS. 7A–7B are diagrammatic cross-sectional views of alternate pinhole geometries for the gas-diffusion control member of FIG. 6.
Figure 7B:
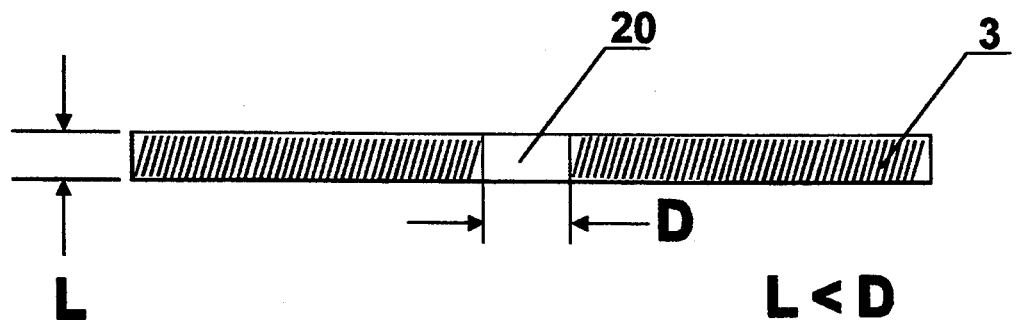

An alternative embodiment of the present invention is shown in FIGS. 6, 7A, and 7B, inclusive. In the embodiment of FIG. 6, all of the members are identical to the embodiment of FIG. 3, except for the gas-diffusion control member (3), which has been replaced by a plurality of gas-diffusion control members (15), (16), (17), (18), and (19), respectively. However, as noted earlier, only one gas-diffusion control member is essential to practice the invention. The gas-diffusion control members (15), (17), and (19) are porous members with a uniform porosity (a fixed diffusion resistance) throughout their length, whereas control members (16) and (18) are subdivided to form separate diffusion zones (11), each of which is characterized by having one or more pinholes (20). Each pinhole (20) may be of any desired geometry, with a maximum cross-sectional diameter of no more than 0.6 mm, and preferably between 0.1 mm to 0.4 mm in diameter. The length or thickness of each pinhole (20) should be diminutive relative to its diameter, with a length-to-diameter ratio of $\leq 1$. If the pinholes (20) are greater than 0.6 mm in diameter, the gas diffuses too fast over too small of an area, relative to the total cell area, to provide an accurate, visual, color reaction indicative of an exposure dosage of a polluting gas. The number of holes (20) and their size determines the diffusion resistance. For very tiny pinholes (20), as would be formed by a laser, a much greater number is necessary to control diffusion resistance. The hole geometry shown in FIG. 7A results from a puncture, whereas the uniform hole geometry of FIG. 7B is more desirable, but more expensive to form. The diameter (D) must be no larger than 0.6 mm, and the length-to-diameter ratio should be $\leq 1$. The number of holes (20) and their size may be varied to provide a diffusion resistance relationship from zero percent (0%) to one hundred percent (100%) diffusion resistance. An example of the present invention, using the embodiment of FIG. 6 for detecting carbon monoxide, is hereinafter described as Example II.

EXAMPLE II

The exposimeter (1) of FIG. 6 comprises a transparent base (8) and a cover (7) secured to the base (8) for forming an enclosure (10), including a color-forming indicator member (2) a flexible, plastic member (4) with openings (9), and an arrangement of diffusion control members (15), (16), (17), (18), and (19), respectively. The diffusion control members (15) and (17) have uniform porosity along each of the six diffusion zones (11). The diffusion control member (16) has five diffusion zones (11), with each defined by a series of tiny holes with a diameter approximately 0.2 mm in size, engraved in each of the diffusion zones (11) in a preselected manner. The first and second zones of the top of the members have one hole, the third zone has two holes, the fourth zone has three holes, and the fifth zone has eight holes. The diffusion control member (18) is similar to member (16), except that the third zone has one hole, the fourth zone has two holes, and the fifth zone has six holes. The diffusion control member (19) has two diffusion zones of uniform porosity. Enclosure (10) is encapsulated between the top cover (7) and the transparent base (8).

The color-forming member (2) is based on the known color-forming reaction between carbon monoxide and palladium salts. The color of the member (2) changes from yellowish-brown to black upon exposure to carbon monoxide. The range of exposure is from 5 ppm per hour to 300 ppm per hour.

Another embodiment of the present invention is shown in FIG. 8 using a combination of gas-diffusion control members, as shown in FIGS. 5 and 6. The gas-diffusion control member (3a) in FIG. 8 is identical to gas-diffusion control member (3a) in FIG. 5, and to gas-diffusion control member (15) in FIG. 6. Gas-diffusion control member (22) contains multiple pinholes (20) in an arrangement with the top zone (11) having one pinhole, the second zone having three pinholes, and the third zone having six pinholes, each having a maximum pinhole size of less than 0.6 mm in conformity with the pinhole requirements for FIG. 6.

An example of the present invention using the embodiment of FIG. 8 for the detection of $H_2S$ is hereinafter described in Example III.

EXAMPLE III

The exposimeter (1) of FIG. 8 comprises a base (8) and a cover (7) secured to the base (8) for forming an enclosure (10), including a color-forming indicator member (2), a porous, plastic-diffusion control member (3a), a flexible, plastic member (4) with openings (9), and an arrangement of diffusion control members (21), (22), and (23). The diffusion control member (3a) has a uniform porosity along the six diffusion zones (11). The diffusion control member (21) has six diffusion zones (11), with diffusion resistance ranging from ten percent (10%) to ninety percent (90%). The diffusion control member (22) has three diffusion zones (11), with one, three, and six tiny pinholes in each diffusion zones, and the diffusion member (23) has only one diffusion zone with twenty percent (20%) diffusion resistance. Enclosure (10) is encapsulated between the top cover (7) and the base (8).

The color-forming member (2) is based on the known color-forming reaction between hydrogen sulfide and lead acetate. The color of the member (2) changes from white to black upon exposure to hydrogen sulfide. The range of exposure is from 5 ppm per hour to 300 ppm per hour.

The optional plastic member (4) should preferably be located between the color-forming indicator (2) and the top cover (7), with the gas-diffusion control member(s) (3) located on either side of the color-forming indicator (2). The openings (9) in the plastic member (4) have a predetermined length corresponding to the thickness of the plastic member (4), and should typically be between 1 mm to 0.25 inches in length. The openings (9) function to collimate the exposed ambient air passing through the enclosure (10) from the openings (9a) in the top cover (7), and form fixed diffusion chambers. The diffusion chambers are defined by the area and length of the openings (9) in the plastic member (4). A diffusion length of at least 1 mm is necessary to deplete the diffusion stream all over the diffusion zone, whereas a minimum length of 2 mm is preferred. As the length of the plastic member (4) increases, its diffusion resistance also increases. The diffusion resistance through the plastic member (4), in combination with the gas diffusion control members (3), controls the colorimetric sensitivity of the exposimeter (1).

If the openings (9) in the plastic member (4) are arranged in series and in alignment with the openings (9a) of the top cover (7), then the diffusion resistance through the plastic member (4) is governed by Fick's First Law of Diffusion, with each opening (9) constituting a chamber of fixed geometry, as follows.

According to Fick's First Law of Diffusion, for each chamber in the series, the mass of pollutant transported by diffusion is $$M = 1/K(CT) \tag{1}$$

where M = mass of pollutant transported across the diffusive resistance K
C = mean concentration acting on the device
T = time of exposure
K = diffusive resistance
On the other hand, $$K = L/AD \tag{2}$$

where A = cross-sectional area of the diffusion path
L = length of the diffusion path or thickness of a porous material used as diffusive resistance
D = diffusion coefficient of the diffusing pollutant through the chamber or porous material Since the dimensions of each of the openings (9) are identical, A and L are constants and a threshold diffusion resistance (K) is established for each opening (9) in the plastic member (4). The colorimetric effect above this threshold diffusion resistance is, therefore, primarily dependent upon the gas-diffusion control member(s) (3).

A multiple number of diffusion zones (11) of at least four, preferably six, is necessary to provide an adequate number of ranges of exposure dosage in ppm per hour for any specific contaminant. Each of the diffusion zones (11) may be calibrated to provide specific CT values, which vary from one another in a given relationship, such as, e.g., by fifty percent (50%), to provide a sufficient graded color sensitivity in the color-forming indicator (2).

What we claim is:

1. A direct-read exposimeter for detecting a specified polluting gas in the ambient atmosphere and for providing a visual, graded measurement of color variation corresponding to different ranges of exposure to said polluting gas over a given time period, said direct-read exposimeter comprising: a base composed of a gas-impermeable, inert material; a cover for said base composed of a gas-impermeable, inert material, with said cover secured to said base along preselected edges to form an enclosure; a color-forming member located in said enclosure adjacent to said base, said color-forming member containing a chromophoric reagent which changes color when exposed to said polluting gas; and at least one gas-diffusion control member disposed between said color-forming member and said cover, with said gas-diffusion control member composed of a porous medium having a multiplicity of solid nonporous ink spots disposed on said porous medium in an arrangement defining a preselected number of separate diffusion zones, with each diffusion zone having a diffusion resistance corresponding to the density of ink spots in said zone, and with said cover having a number of openings in alignment with each of said diffusion zones for exposing each of said diffusion zones to the ambient atmosphere.

2. A direct-read exposimeter, as claimed in claim 1, wherein said gas-diffusion control member includes at least four separate diffusion zones, with said multiplicity of solid, nonporous ink spots arranged in said diffusion zones in a pattern corresponding to halftone printing.

3. A direct-read exposimeter, as claimed in claim 2, wherein said density of ink spots in each diffusion zone varies based on either the spacing between said ink spots, the size of said ink spots, or both.

4. A direct-read exposimeter, as claimed in claim 3, wherein said enclosure further comprises a member of predetermined thickness disposed between said color-forming member and said cover, and having a preselected number of openings of predetermined size arranged in alignment with said openings in said cover, for forming predetermined diffusion channels for diffusing said polluting gas.

5. A direct-read exposimeter, as defined in claim 4, wherein said base includes a plurality of openings corresponding to the number of said openings in said cover, and arranged in alignment therewith, and in alignment with the openings in said member of predetermined thickness.

6. A direct-read exposimeter, as defined in claim 4, wherein the openings in said cover and the openings in said member are of predetermined thickness arranged in a linear series.

7. A direct-read exposimeter, as defined in claim 4, further comprising a plurality of gas-diffusion control members in a predetermined, overlapping relationship.

8. A direct-read exposimeter for detecting a specified polluting gas in the ambient atmosphere and for providing a visual, graded measurement of color variation corresponding to different ranges of exposure to said polluting gas over a given time period, said direct-read exposimeter comprising: a base composed of a gas-impermeable, inert material; a cover for said base composed of a gas-impermeable, inert material, with said cover secured to said base along preselected edges to form an enclosure; a color-forming member located in said enclosure adjacent to said base, said color-forming member containing a chromophoric reagent which changes color when exposed to said polluting gas; and at least one gas-diffusion control member disposed between said color-forming member and said cover, with said gas-diffusion control member composed of a nonporous medium having multiple pinholes in an arrangement defining a preselected number of separate diffusion zones, with each pinhole in each diffusion zone having a maximum diameter of 0.6 mm, and a length-to-diameter ratio of $\leq 1$, and with each diffusion zone having a diffusion resistance based upon the number of pinholes and the size of each pinhole in said zone and wherein said cover has a number of openings in alignment with each of said diffusion zones for exposing each of said diffusion zones to the ambient atmosphere.

9. A direct-read exposimeter, as defined in claim 8, wherein said gas-diffusion control member has at least four separate diffusion zones, with at least one pinhole in each zone.

10. A direct-read exposimeter, as defined in claim 9, wherein said enclosure further comprises a member of predetermined thickness disposed between said color-forming member and said cover, and having a preselected number of openings of predetermined size arranged in alignment with said openings in said cover.

11. A direct-read exposimeter, as defined in claim 10, wherein said base includes a plurality of openings corresponding to the number of said openings in said cover, and arranged in alignment therewith, and in alignment with the openings in said member of predetermined thickness.

12. A direct-read exposimeter, as defined in claim 10, wherein the openings in said cover and the openings in said member of predetermined thickness are arranged in a linear series.

13. A direct-read exposimeter, as defined in claim 10, further comprising a plurality of gas-diffusion control members in a predetermined, overlapping relationship.

14. A direct-read exposimeter for detecting a specified polluting gas in the ambient atmosphere and for providing a visual, graded measurement of color variation corresponding to different ranges of exposure to polluting gas over a given time period, said direct-read exposimeter comprising: a base composed of a gas-impermeable, inert material; a cover for said base composed of a gas-impermeable, inert material, with said cover secured to said base along preselected edges to form an enclosure; a color-forming member located in said enclosure adjacent to said base, said color-forming member containing a chromophoric reagent which changes color when exposed to said polluting gas; and at least one gas-diffusion control member disposed between said color-forming member and said cover, with said gas-diffusion control member composed of at least one porous medium having multiple nonporous ink spots for defining at least one diffusion zone, with a diffusion resistance corresponding to the density of said ink spots in said zone, and at least one nonporous medium having one or more diminutive pinholes, with a maximum pinhole size below 0.6 mm, for defining at least one other diffusion zone, having a diffusion resistance based on the number and size of said pinholes in said other diffusion zone and wherein said cover has a number of openings in alignment with each of said diffusion zones for exposing each of said diffusion zones to the ambient atmosphere.

15. A direct-read exposimeter, as defined in claim 14, wherein said porous medium contains a multiple number of said nonporous ink spots arranged to form multiple diffusion zones, and wherein said nonporous medium contains at least a plurality of said pinholes arranged to form separate diffusion zones, with said porous medium and said nonporous medium arranged in an overlapping relationship.

16. A direct-read exposimeter, as defined in claim 15, wherein said enclosure further comprises a member of predetermined thickness disposed between said color-forming member and said cover, and having a preselected number of openings of predetermined size arranged in alignment with said openings in said cover.

17. A direct-read exposimeter, as defined in claim 15, wherein said base includes a plurality of openings corresponding to the number of said openings in said cover, and arranged in alignment therewith, and in alignment with the openings in said member of predetermined thickness.

18. A direct-read exposimeter, as defined in claim 15, wherein the openings in said cover and the openings in said member of predetermined thickness are arranged in a linear series.

19. A direct read exposimeter as defined in claim 8 wherein said gas diffusion control member has six or less pinholes.

* * * * *